United States Patent [19]

Kato

[11] Patent Number: 4,608,472
[45] Date of Patent: Aug. 26, 1986

[54] METHOD OF AND APPARATUS FOR STERILIZING DEVICES

[75] Inventor: Yasuaki Kato, Hiroshima, Japan

[73] Assignee: Japan Medical Supply Co Ltd, Hiroshima, Japan

[21] Appl. No.: 583,328

[22] Filed: Feb. 24, 1984

[30] Foreign Application Priority Data

Mar. 14, 1983 [JP] Japan ................................ 58-40818
Apr. 21, 1983 [JP] Japan ................................ 58-58797
Aug. 30, 1983 [JP] Japan ................................ 58-159951

[51] Int. Cl.$^4$ ............................................. H05B 6/64
[52] U.S. Cl. ................................ 219/10.43; 219/10.41; 219/10.57
[58] Field of Search ............... 219/10.57, 10.77, 10.41, 219/10.43, 10.79, 10.67, 10.49 R, 10.75; 340/686, 687; 422/21, 22; 250/206, 215, 578; 433/28, 32, 61

[56] References Cited

U.S. PATENT DOCUMENTS 2,513,778  7/1950  Bailey ........................... 219/10.49 R
2,596,770  5/1952  Groven ............................. 219/10.79
4,492,840  1/1985  Lex .................................. 219/10.57

Primary Examiner—Clarence L. Albritton
Assistant Examiner—M. M. Lateef
Attorney, Agent, or Firm—Cushman, Darby & Cushman

[57] ABSTRACT

A sterilization method and apparatus comprise a coil connected to a high-frequency current generating source to generate a magnetic field in which a device to be sterilized is disposed so that an eddy current is generated in a conductor forming the device or a conductor disposed in the vicinity of the device due to the electromagnetic induction action, whereby bacteria attached to the device is sterilized by heat produced by the eddy current loss. The sterilization method and apparatus is suitable for a device such as a tubular connector for connecting between the abdominal cavity and a disposable container containing a dialysate in the peritoneal dialysis, specifically the continuous ambulatory peritoneal dialysis and which is repeatedly used while exchanging the container.

10 Claims, 9 Drawing Figures

METHOD OF AND APPARATUS FOR STERILIZING DEVICES

TECHNICAL FIELD OF THE INVENTION

The present invention relates to a method of and an apparatus for sterilizing devices, and more particularly to a method of sterilizing devices into an aseptic condition and an apparatus therefor.

DESCRIPTION OF THE PRIOR ART

Medical devices containing medical materials are required to be in an aseptic condition when used, and each device is sterilized before use. The sterilization treatment is made by methods using radiation, liquid chemicals, heat or the like. Radiation and ethylene oxide gas are conventionally known to be suitable for sterilizing disposable devices. However, such methods are not suitable for sterilizing reusable devices, require large equipment, and are not suitable for a personal use.

Heretofore, reusable medical devices which are required to be sterilized each time they are used have been generally disinfected using liquid chemicals.

For example, the increasingly popular peritoneal dialysis treatment requires a simple device as compared with an artificial kidney. The expense for the treatment is extremely economical and a patient's charge is greatly reduced. A continuous ambulatory peritoneal dialysis method is now available and, consequently, the patient can even work while continuously receiving the treatment. The reliability of this dialysis method is dependent on the prevention of bacteria from entering into the dialysis tube and the sterilization treatment of the connector which connects the dialysis tube attached to the abdominal region and a disposable container containing the dialysate. In other words, the peritoneal dialysis method utilizes the dialysis tube attached to the abdominal region which is connected to the disposable container containing the dialysate so that the dialysate is injected into the abdominal cavity from the container through the tube to make the dialysis through the peritoneum between capillaries in the peritoneum and the abdominal cavity. The dialysate is exchanged about three times a day. Each time the dialysate is exchanged, the container containing the old dialysate is removed from the tube attached to the abdominal region and is exchanged for a new container. At this time, since the connector portion of the tube is exposed to the outside air, there is a possibility of bacterial contamination of the connector portion. When a new container is, therefore, connected to the tube, it is necessary to sterilize the connector portion. Specifically, the abdominal cavity does not have the ability of defending against bacteria and thus significant risks of the patient contracting peritonitis is presented when bacteria enters the abdominal cavity. Accordingly, the connector portion must be perfectly sterilized to prevent bacteria from entering to the cavity prior to its connection to the tube.

However, although disinfection using liquid chemicals mentioned above is relatively simple, there exist bacteria which are resistant to the liquid chemicals. Furthermore, side effects from using the chemicals could be experienced by the patient. Accordingly, it is necessary to perfectly prevent bacteria from entering the peritoneal cavity.

Recently, a thermal sterilization method has been studied as a solution to such problems. However, steam sterilization which is a type of thermal sterilization also requires large equipment in the same manner as radioactive sterilization. Further, although flame sterilization using an alcohol lamp or the like has been used flame sterilization is inherently dangerous due to the exposed flame that is required. Sterilization may also not be complete utilizing the flame technique if the operator does not possess a certain degree of skill.

SUMMARY OF THE INVENTION

It is an object of the present invention to, in view of the conventional drawbacks, provide an improved relatively simple sterilization method and apparatus capable of being used by unskilled persons suitable for repeated sterilization of devices, in which the sterilization treatment can be made reliably and economically with less danger.

It is another object of the present invention to provide a tubular connector for a sterilization apparatus capable of effectively sterilizing only a portion to be sterilized of the tubular connector which is required to be sterilized.

It is still another object of the present invention to provide a sterilization apparatus suitable for receiving a tube and a tubular connector of devices to be sterilized so that they are effectively sterilized.

According to a method of the present invention, a conductor disposed adjacent to devices is located within a magnetic field produced by a high frequency current so that bacteria attached to the devices are reliably sterilized by heat due to an eddy current generated in the conductor, that is, high-frequency inductive heating.

Further, according to a method of the present invention, devices to be sterilized which are formed of a conductor are disposed within a magnetic field generated by a high-frequency current so that the devices on which microorganisms are attached are completely sterilized by heat due to an eddy current generated in the conductor forming the devices.

According to an apparatus of the present invention, a coil connected to high-frequency current generating means generates a magnetic field and devices to be sterilized are received in a sterilizing chamber around which the coil is wound so that the devices are sterilized by the high-frequency inductive heating.

Further, according to the present invention, the device to be sterilized is a tubular connector, of which only a portion to be sterilized is formed of a conductor.

According to the present invention, a coil is bent at its middle portion so that a tubular connector is easily received in a sterilizing chamber around which the bent coil is wound.

BRIEF DESCRIPTION OF THE ACCOMPANYING DRAWINGS

The above and other objects and features of the present invention will be more apparent from the following detailed description given with reference to the accompanying drawings, in which:

FIG. 1 is a perspective view of a sterilization apparatus showing one embodiment of the present invention;

FIGS. 2(A) and 2(B) are a perspective view and a cross-sectional view showing an example of a device to be sterilized by the sterilization apparatus of the present invention, respectively;

DESCRIPTION OF THE PREFERRED EMBODIMENTS

Figure 1:
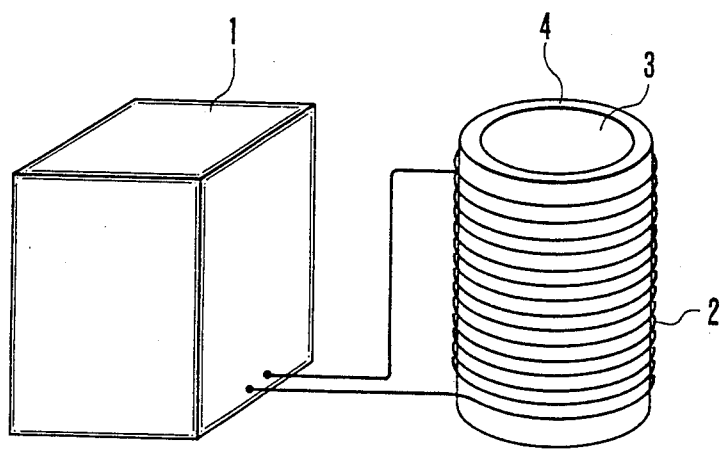

Referring to FIG. 1, a sterilization apparatus of the present invention includes a high-frequency current generating source 1 for generating a high-frequency current. A coil 2 is wound on the outside periphery of a cylindrical member 4 forming a sterilization chamber 3. The coil 2 is connected to the high-frequency current generating source 1 and generates a magnetic field due to the high-frequency current supplied from the source 1.

In order to sterilize a medical device by means of the sterilization apparatus constructed above, the medical device is placed within the sterilization chamber 3 together with a conductor element and the high-frequency current source 1 is operated to supply the high-frequency current to the coil 2. An eddy current is generated in the conductor element by the electromagnetic induction action due to the magnetic field generated by the coil 2. The conductor element is thus heated to a high temperature due to the eddy current loss. Consequently, the medical device place within the chamber 3 together with the conductor element disposed adjacent to the device is also heated to a high temperature, so that the device to which bacteria are attached can be reliably sterilized. In this case, the medical device is formed of an insulator. However, if the medical device is formed of a conductor material (such as the device d shown in FIGS. 2(A) and 2(B)), it is not necessary to place the conductor element into the chamber 3 together with the device and thus only the medical device D need be placed into the chamber 3. In this case, an eddy current is generated in the conductor material forming the medical device D so that the conductor material is heated to a high temperature and the medical device is thus sterilized. In the case where the medical device is formed of a conductor, only a desired portion thereof, that is, a portion required to be sterilized may be formed of a conductor so that only the desired portion can be selectively sterilized.

The conductor is desirably formed of iron, nickel, cobalt, or an alloy including such metals and preferably exhibits superior resistance to high temperatures and is thus not oxidized or deteriorated at high temperatures. In order to completely sterilize medical devices, it is desirable to heat the medical devices at a temperature of 200° C. or more in a predetermined time. In order to satisfy such a heating condition, it is considered that the magnetic flux density of the high frequency magnetic field of 10 gausses or more is proper. This value is dependent on the material, shape, size and the like of the medical device to be sterilized and can be selected to be suitable for each device to be sterilized. The high-frequency current generating source 1 described above may be one which is used in a known high-frequency induction heating device and the performance of the source can be determined from the sterilization temperature and time on the basis of the flux density, the material, the shape and the size of the device in association with the inductance of the coil 2. The cylindrical member 4 forming the chamber 3 is formed with at least one open end and is formed of a nonconductive, heat-resistant material such as ceramic or heat-resistant plastic. Although the chamber 3 may be formed on the peripheral portion of the coil 2 instead of being formed within the coil, a large loss is suffered with regard to the heat efficiency.

One example where a device was sterilized by using the sterilization apparatus is now described.

EXAMPLE

Figure 2A:
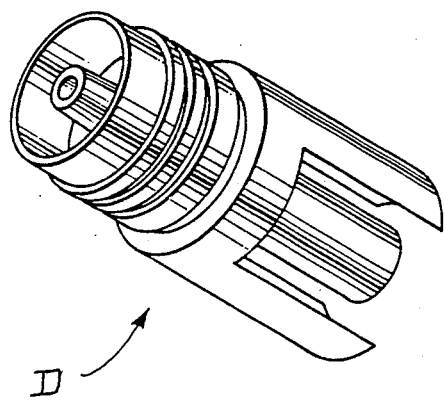
Figure 2B:
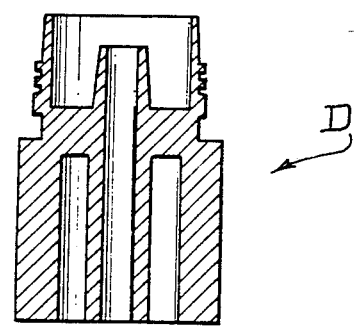

An output power and a frequency of the high-frequency current generating source 1 were 135 watts and 10 KHz, respectively, and the magnetic flux density of the coil 2 at this time was maximum 500 gausses. A tubular connector, as shown in FIGS. 2(A) and 2(B), formed of ferritic stainless steel and which is actually used in the peritoneal dialysis was used as a device to be sterilized. In order to confirm the sterilization ability, the indicator bacteria of $10^5$ were attached on the inner side of the connector, and then the connector was set in the chamber 3. A time required to sterilize all the indicator bacteria to death was measured. This measured value was compared with times required to sterilize all the indicator bacteria to death by means of a flame sterilization and liquid chemicals disinfection using an undiluted solution of ISODINE ®, respectively. In this case, as the indicator bacteria, the spore of *B. Stearothermophillus* was used as the most heat-resisting bacteria and the spore of *B. Subtilis* was used as the bacteria which is the most resistant to disinfectants. The following table shows the experimental results.

TABLE

| | Time Required To Sterilize All The Indicator Bacteria | |
|---|---|---|
| | B. Stearothermophillus | B. Subtilis |
| Sterilization by the present invention | 10 seconds | 10 seconds or less |
| Flame Sterilization | 15 seconds | 15 seconds |
| Disinfection Using Liquid Chemicals | Not sterilized in 30 seconds | Not sterilized in 30 seconds |

As seen from this table, the high-frequency induction heating sterilization according to the present invention is rapidly and completely effected as compared with the flame sterilization and the sterilization using liquid chemicals. Furthermore, there is no danger such as a fire and a burn in the flame sterilization, and a patient can easily use it by oneself. The sterilization apparatus and the device can be also used repeatedly. In this repeated use, the high-frequency current generating source 1 may be provided with a timer unit and a current limitation circuit to maintain the sterilization time and the current constant so that the sterilization treatment can be uniformly and completely performed. Further, as described above, since only the portion necessary to be sterilized in the device can be formed of a conductor to selectively sterilize only the portion, a portion for which the sterilization treatment is structurally difficult by means of the flame sterilization or the sterilization using liquid chemicals can be extremely easily sterilized by the sterilization method and apparatus of the present invention.

Figure 3:
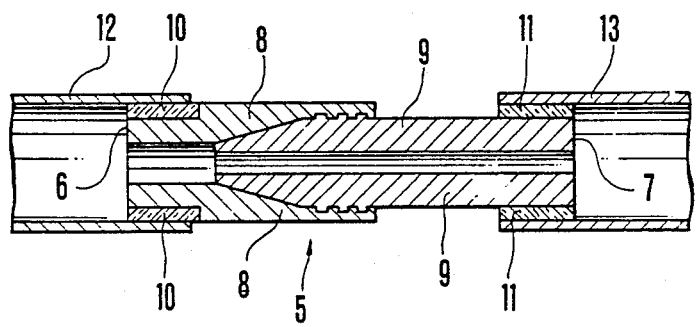
FIGS. 3 and 4 are cross-sectional views of tubular connectors to be sterilized by the sterilization apparatus of the present invention, respectively.
Figure 4:
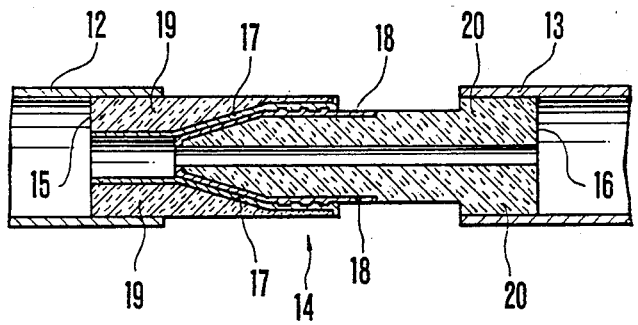

FIGS. 3 and 4 respectively show medical tubular connectors 5 and 14 which are sterilized by the sterilization method and apparatus of the present invention. The connector 5 shown in FIG. 3 includes a female connector 6 and a male connector 7 most of which are formed of conductors 8 and 9, respectively, and only those portions 10, 11 coupled to tubes 12 and 13 are formed of heat-insulating materials. The connector 14 includes a female connector 15 and a male connector 16 of which only those surfaces coming into contact with each other are formed of conductors 17 and 18 and most of which are formed of heat-insulating materials 19 and 20 to which tubes 12 and 13 are connected, respectively.

The tubular connectors 5 and 14 constructed above contain the conductors 8, 9, 17 and 18 in which an eddy current is generated when the connectors 5 and 14 are disposed in the sterilization chamber 3 to receive the magnetic field generated from the coil 2, so that the conductors can be heated to sterilize the connectors. Although the connector includes relatively complicated connecting portion and it is difficult to sterilize the inside portion of the female connector, even such a portion can be completely and quickly sterilized by the sterilization method of the present invention if the portion is at least formed of a conductor.

In FIGS. 3 and 4, there are shown the connectors coupled to each other. The sterilization treatment of the connector may be made just before or after coupling the connector. The bonding between the conductor and the heat-insulating material in the connector is made by methods, for example, of force-fitting the conductor into the heat-insulating material, using an adhesive, welding the conductor to the material, or the like in the case of the structure shown in FIG. 3, while it is made by, for example, plating, evaporation, or coating in the case of the structure shown in FIG. 4. The above description was directed to the situation where both the female and male connectors are sterilized. However, if only one of the connectors is repeatedly used and the other is used only one time, only one connector used repeatedly may be formed of a conductor as described above. The connection between a female connector and a male connector can be made, for example, by screws, by fitting projections to grooves, by fittingly inserting one to the other, by attracting one to the other by means of a magnet, or the like, and a mechanism for locking the connection portion may be provided in the connector.

In FIGS. 3 and 4, if the tube is not formed of a heat-resisting material, it is desirable that the portion of the connector which is connected to the tube is formed of a heat-resisting, heat-insulating material such as ceramic, glass, heat-resisting plastic, silicone rubber and cork.

The tubular connector is suitable for the connection of the tube for coupling the abdominal cavity to the dialysate container in the above-mentioned peritoneal dialysis, specifically the continuous ambulatory peritoneal dialysis and which is repeatedly used while exchanging the container and is useful for the repeated use by sterilizing it by means of the sterilization method and apparatus of the present invention.

Figure 5:
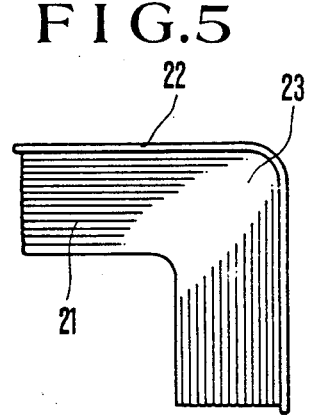
FIGS. 5 and 6 are a side view and a perspective view showing a modification of a coil used in the sterilization apparatus of the present invention, respectively.
Figure 6:
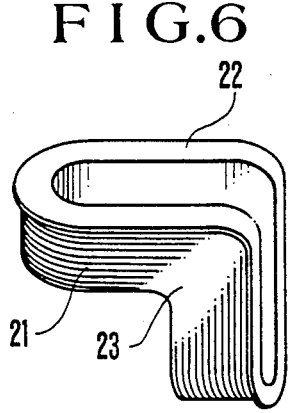
Figure 7:
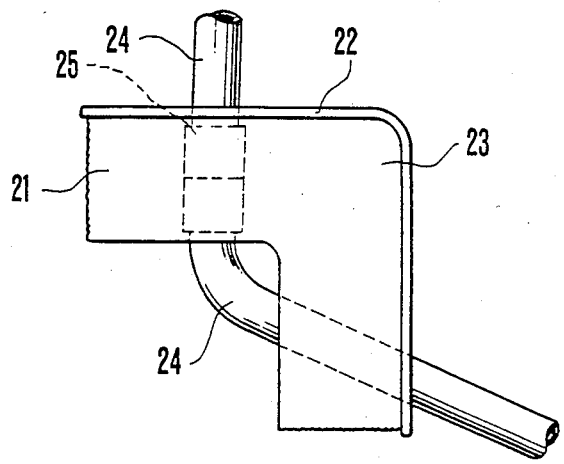
FIG. 7 is a side view showing an aspect of the coil in use.

A coil 21 shown in FIGS. 5 and 6 is bent at the middle of the coil 2 shown in FIG. 1 to be L-shaped and is wound on a supporting member 22. As described above, in the peritoneal dialysis, a straight tube or a tubular connector is used to connect the abdominal cavity with the dialysate container. Furthermore, a tube or a tubular connector is used for the transfusion and the infusion. Since such a tube or a tubular connector is straight, it is relatively difficult to set it in the sterilization chamber 3 around which the cylindrical coil 2 is wound as shown in FIG. 1. In order to solve this problem, the coil 21 shown in FIGS. 5 and 6 is bent at its middle portion so that a connector 25 coupling between tubes 24 is easily set within the coil 21 as shown in FIG. 7. The connector 25 can be reliably prevented from being contaminated after sterilization by sterilizing the connector in the coupled state as compared with the case where the connector is coupled after sterilization.

In the case of the coil 21 shown in FIGS. 5 and 6, since the magnetic field is rather weak in the vicinity of the bent portion 23 of the coil 21, it is desirable that the device such as the connector is disposed at a portion of coil 23 other than the bent portion 23 as shown in FIG. 7. The bent portion 23 may be gradually bent over a wide range or sharply bent in a narrow range. Although the bent angle is not limited to a specific angle, it is desirable that the angle be about 90° so that, the L-shaped configuration is formed. Such an L-shaped configuration is particularly effective for sterilization.

Figure 8:
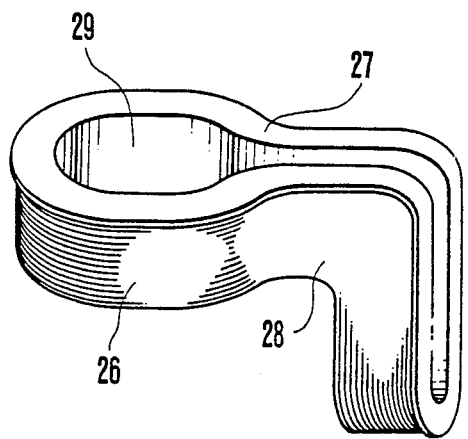
FIG. 8 is a perspective view showing another modification of the coil used in the sterilization apparatus of the present invention.

FIG. 8 shows a coil 26 having another shape, which is wound on a supporting member 27 and contains a sterilization chamber 29 which is widely formed in one end extending away from a bent portion 28 (i.e. to left horizontally as viewed in FIG. 8), so that the connector 25 coupling the tubes 24 as shown in FIG. 7 can be easily received in the chamber 29.

The foregoing description and the embodiments are provided for the purposes of illustrating the invention but is not considered to limit the scope thereof in any way. Clearly, numerous additions, modifications and other changes can be made to the present invention without departing from the scope thereof as set forth in the claims.

What is claimed is:

1. A method of heat-sterilizing a device comprising the steps of:

disposing a conductor element near said device;

exposing said conductor element to a magnetic field generated by a coil connected to a high-frequency current, said coil being shaped generally as an ellipse bent at substantially a right angle, having a vertical and a horizontal side, one side being of an enlarged inside diameter compared with another side; and allowing an eddy current to be generated in said conductor element to responsively heat the conductor element and then allowing the generated heat to be transferred to the device thereby heat-sterilizing the device.

2. A method of heat-sterilizing a device comprising the steps of:

forming said device of a conductor material;

exposing said device to a magnetic field generated by a coil connected to a high-frequency current, said coil being shaped generally as an ellipse bent at substantially a right angle, having a vertical side and a horizontal side, one side being of an enlarged inside diameter compared with another side; and allowing an eddy current to be generated in said conductor material of said device so that the device is sterilized by heat produced by the eddy current.

3. A method according to claim 1, wherein said device is a tubular connector.

4. A method according to claim 3, wherein said tubular connector is used in the peritoneal dialysis.

5. An apparatus for the heat-sterilization of a device comprising:
   current-generating means for generating a high-frequency current;
   a coil connected to said high-frequency current generating means to generate a magnetic field in response to the supplied high-frequency current, said coil being shaped generally as a ellipse bent at substantially a right angle, having a vertical and a horizontal side; and
   a sterilization chamber around which said coil is wound for receiving said device, said sterilization chamber being formed at one side of said coil with the inside diameter of said one side being enlarged as compared to the inside diameter of another portion of said coil.

6. An apparatus according to claim 5 further comprising means disposed in the vicinity of said device in said chamber for generating an eddy current when exposed to said magnetic field to thereby produce heat so that said device is sterilized by the produced heat.

7. An apparatus according to claim 5, wherein said device consists essentially of conductor material and wherein said device is sterilized by heat produced by an eddy current generated in said conductor material in response to exposure to said a magnetic field produced by said coil.

8. An apparatus according to claim 5, wherein a portion of said device to be sterilized consists essentially of a conductor material and wherein said device is sterilized by heat produced by an eddy current generated in said portion in response to exposure to said magnetic field produced by said coil.

9. An apparatus according to claim 5, wherein said device is a tubular connector.

10. An apparatus according to claim 9, wherein said tubular connector is a connector used in the continuous ambulatory peritoneal dialysis.

* * * * *